(12) United States Patent
Cai et al.

(10) Patent No.: US 6,333,435 B1
(45) Date of Patent: Dec. 25, 2001

(54) PROCESS OF SYNTHESIZING BINAPHTHYL DERIVATIVES

(75) Inventors: Dongwei Cai, Edison; David L. Hughes, Old Bridge, both of NJ (US); Sylvain Levac, Cap-Rouge (CA); Thomas R. Verhoeven, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/443,616

(22) Filed: May 18, 1995

(51) Int. Cl.$^7$ ....................................... C07F 9/02
(52) U.S. Cl. .................. 568/17; 560/100; 568/808
(58) Field of Search .................. 568/10, 17, 808; 560/100; 556/21

(56) References Cited

U.S. PATENT DOCUMENTS

| | | | |
|---|---|---|---|
| 3,668,086 | * 6/1972 | Hughes | 556/21 |
| 3,676,481 | * 7/1972 | Chia | 556/21 |
| 4,604,474 | * 8/1986 | Kumobayashi et al. | 556/23 |
| 4,605,750 | * 8/1986 | Kumobayashi et al. | 556/23 |
| 4,691,037 | 9/1987 | Yoshikawa et al. | 556/18 |
| 4,739,084 | * 4/1988 | Takaya et al. | 556/21 |
| 4,764,629 | * 8/1988 | Sayo et al. | 556/23 |
| 4,766,227 | * 8/1988 | Sayo et al. | 556/21 |
| 4,879,416 | 11/1989 | Puckette et al. | 568/13 |
| 4,956,055 | 9/1990 | Puckette | 204/72 |
| 5,026,886 | 6/1991 | Stavinoha et al. | 556/70 |
| 5,231,202 | 7/1993 | Hayashi et al. | 556/21 |
| 5,268,492 | 12/1993 | Yamamoto et al. | 549/460 |
| 5,274,146 | * 12/1993 | Ishizaki et al. | 556/14 |
| 5,286,888 | * 2/1994 | Sano et al. | 556/21 |
| 5,312,939 | 5/1994 | Hori et al. | 556/14 |
| 5,324,870 | * 6/1994 | Sano et al. | 556/21 |
| 5,399,771 | * 3/1995 | Cai et al. | 568/17 |

OTHER PUBLICATIONS

Journal of Organic Chemistry, "Synthesis of Chiral . . . Insertion", vol. 59, pp. 7180–7181, Cai et al., Sep. 1994.*
JACS, vol. 93, No. 22, pp. 5908–5910 (Aug. 1971), Semmelhack, et al.
Tetrahedron Letters, vol. 34, No. 10, pp. 1615–1616 (Nov. 1993), by T. Ohta, et al.
JACS, vol. 98, No. 23, pp. 7255–7265 (Apr. 1976), by Komiya, et al.
J. Org. Chem. vol. 58, pp. 1945–1948 (Aug. 1993), by Y. Uozumi, et al.
Bull. Chem. Soc. vol. 66, No. 7, pp. 2202–2205, M. Kawashima, et al., Jul. 1993.
J. Am. Chem. Soc., vol. 102, pp. 4933–4941 (Feb. 1980), by A. Gillie, et al.
Tetrahedron Letters, vol. 31, No. 44, pp. 6321–6324 (Aug. 1990), by L. Kurz, et al.

* cited by examiner

*Primary Examiner*—Robert Dawson
(74) *Attorney, Agent, or Firm*—Sylvia A. Ayler; Mark R. Daniel

(57) ABSTRACT

A process of synthesizing a compound of the formula 1:

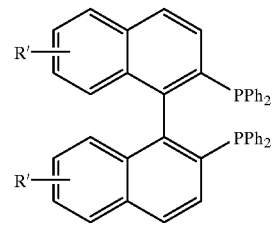

is disclosed, which comprises reacting a compound of the formula 2:

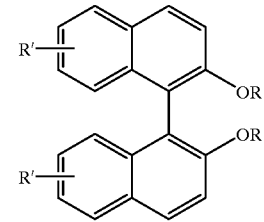

with diphenylphosphine in the presence of an amine base and a nickel catalyst to produce a compound of formula 1.

6 Claims, No Drawings

PROCESS OF SYNTHESIZING BINAPHTHYL DERIVATIVES

BACKGROUND OF THE INVENTION 2,2'-Bis(diphenylphosphino)-1,1'-binaphthyl (BINAP) has become an important chiral ligand for catalytic asymmetric induction. Its wide application has been somewhat limited due to the scarce supply. The present invention relates to a simple and inexpensive process for the synthesis of BINAP derivatives in which the naphthyl groups are substituted, avoiding the necessity of multistep syntheses and minimizing the formation of secondary products.

SUMMARY OF THE INVENTION

A process of synthesizing a compound of formula 1 is disclosed

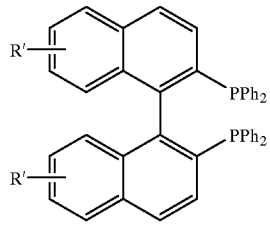

1 wherein each R' is independently selected from the group consisting of: $C_{1-4}$ alkyl, hydroxyl, $C_{1-4}$ alkoxyl, $C_{1-4}$ acyl, carboxyl, $C_{1-4}$ alkoxycarbonyl, —OP and —COOP wherein P is a protecting group, comprising reacting a compound of the formula 2:

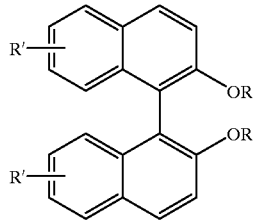

2 wherein R is selected from the group consisting of triflate, mesylate and tosylate, and R' is as defined above, with diphenylphosphine in the presence of an amine base and a nickel catalyst to produce a compound of formula 1.

DETAILED DESCRIPTION OF THE INVENTION

As used herein, the following terms and definitions apply.

The abbreviation "Ph" refers to phenyl. Diphenylphosphine is abbreviated $Ph_2PH$.

BINAP stands for the compound 2,2'-bis(diphenylphosphino)-1,1'-binaphthyl which has the structural formula 1:

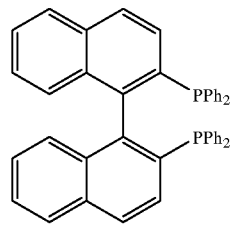

1

BINAP derivatives as used herein refers to BINAP with substituent groups attached to the naphthyl portions of the molecule. The substituent groups can be selected from the group consisting of: $C_{1-4}$ alkyl, hydroxyl, $C_{1-4}$ alkoxyl, $C_{1-4}$ acyl, carboxyl, $C_{1-4}$ alkoxycarbonyl, —OP and —COOP wherein P is a protecting group.

Preferred BINAP derivatives include the following:

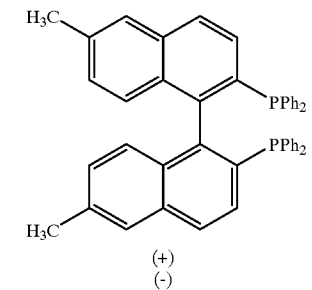

(+)
(-)

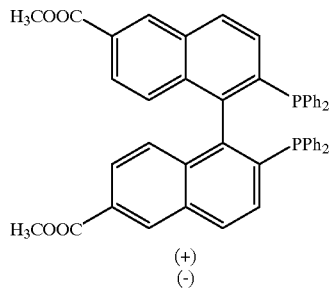

(+)
(-)

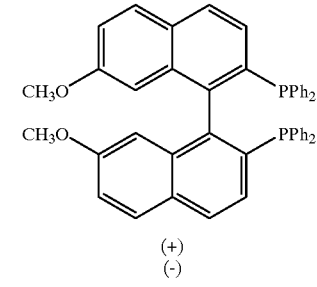

(+)
(-)

Such preferred BINAP derivatives are included in pure form as well as mixtures of isomers.

Alkyl refers to hydrocarbon radicals having 1–4 carbon atoms, which can be straight or branched for the $C_3$ and $C_4$ members of the group.

$C_{1-4}$ acyl refers to the group: $C_{1-4}$ alkyl—C(O)—.

Carboxyl refers to the group: —COOH.

$C_{1-4}$ alkoxycarbonyl refers to the group: $C_{1-4}$ alkyl-O—C(O)—.

In —OP and in —COOP, P represents a protecting group for hydroxyl and carboxyl. These protecting groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable hydroxyl and carboxyl protecting groups are known in the art. See, e.g., T. W. Greene, *Protective Groups in Organic Synthesis,* John Wiley & Sons, Inc., (2nd ed. 1991) (Chapters 2 and 5).

Triflate (OTf) refers to the leaving group trifluoromethane sulfonate.

Mesylate (OMs) refers to the leaving group methanesulfonate.

Tosylate (OTs) refers to the leaving group toluenesulfonate.

The catalyst which is included herein is a nickel catalyst. Such catalysts are selected from the group consisting of: $NiCl_2$.bis(diphenyl)phosphinyl $C_{1-4}$ alkanes, $NiBr_2$, $NiCl_2$, $NiCl_2$-bis(diphenyl)phosphinyl ferrocene, abbreviated $NiCl_2$/dppf; $NiCl_2$-bis(triphenylphosphine), abbreviated $NiCl_2/(Ph_3P)_2$; Ni-tetrakis(triphenylphosphine), abbreviated $Ni(Ph_3P)_4$; Ni-tetrakis(triphenylphosphite), abbreviated $Ni[(PhO)_3]_4$ and Ni-dicarbonyl bis(triphenyl)phosphine, abbreviated $Ni(CO)_2(Ph_3P)_2$.

The preferred catalysts for use herein are the $NiCl_2$.bis (diphenyl)phosphinyl $C_{1-4}$ alkanes. In particular, the $C_{2-3}$ alkanes are preferred. Hence, the preferred catalysts are $NiCl_2$.bis(diphenyl)phosphinylethane, which is abbreviated "$NiCl_2$dppe", and $NiCl_2$.bis(diphenyl)phosphinylpropane, which is abbreviated "$NiCl_2$dppp". The most preferred catalyst for use in the process described herein is $NiCl_2$dppe.

In one embodiment of the invention, an R(+) isomer of the compound of formula 1 is provided. An R (+) isomer of a compound of formula 2:

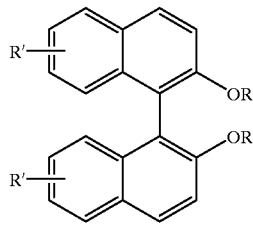

2 wherein R and R' are as previously defined,
is reacted with diphenylphosphine in the presence of an amine base and a nickel catalyst to produce the R (+) isomer of a compound of formula 1.

In another embodiment of the invention, the S (−) isomer of a compound of the formula 2: wherein R and R' are as previously defined, is reacted with diphenylphosphine in the presence of an amine base and a nickel catalyst to produce the S (−) isomer of a compound of formula 1.

One more preferred process which is described herein directly converts the R (+) chiral ditriflate of 1,1'-bi-2-naphthol to R (+) chiral BINAP 1. Likewise, another preferred process directly coverts the S(−) chiral ditriflate of 1,1'-bi-2-naphthol to the (S)-chiral BINAP 1. Essentially no racemization occurs in these preferred embodiments.

Diphenylphosphine is added in a suitable solvent at a temperature which is effective for allowing the formation of BINAP 1 in the presence of an amine-containing base and the nickel catalyst. Since diphenylphosphine is a good ligand for nickel, the amount of diphenylphosphine present in the reaction medium can significantly effect the reaction rate, slowing the reaction if the amount of diphenylphosphine is too great. When the diphenylphosphine is added stepwise during the reaction, the reaction can be completed in about 2 days. The coupling reaction slows down at later stages, possibly due to product and impurity poisoning. The reaction is typically completed in 3~4 days if all the diphenylphosphine is added at once.

Suitable solvents include those which do not substantially oxidize the diphenylphosphine at the appropriate temperature, while maintaining the desired solubility. Polar solvents are preferred. Illustrative of these solvents are dimethylformamide (DMF), acetonitrile and N-methylpyrrolidinone. The most preferred solvent is DMF.

The amine base and amount of base included in the reaction influence the reaction selectivity and reaction rate. Amine bases as used herein include the following: diazabicyclo(2.2.2)octane (DABCO), triethylamine ($Et_3N$), diisopropylethylamine, tri n-propylamine, and tri n-butylamine. The preferred amine bases are DABCO and $Et_3N$. The most preferred base is DABCO.

The reaction is typically run at a temperature which allows the reaction to proceed without producing undesirable quantities of side products. The temperature range is from about 80 to about 120° C., with about 100° C. being preferred. The temperature, time and base which are preferred are dependent upon the starting bis naphthol derivative which is used. When a bis naphthol ditriflate is used as the starting material, the reaction proceeds well using DMF as the solvent and DABCO as the base at a temperature of about 100° C. Generally, the isolated product is crystalline, which is contaminated in minor amounts with a mono-oxide of the formula:

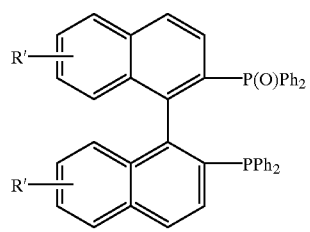

The exclusion of oxygen from the reaction tends to minimize the formation of this side product.

In a particularly preferred embodiment of the invention, the known compound 6-methylnaphthol is reacted to form 6,6'-bismethyl-1,1'-binaphthol (±). The racemic mixture of isomers can be resolved to produce the (+) and (−) isomers in substantially pure form.

Resolution of bisnaphthol and binaphthyl derivatives above can be accomplished using N-benzyl cinchonidinium chloride in CH₃CN or EtOAc.

The 6,6'-bismethyl-1,1'-binaphthol (in substantially pure isomeric form or in racemic mixture) can then be reacted with triflic anhydride (Tf₂O) to produce the bis triflate, which in turn is treated with diphenylphosphine in the presence of a nickel catalyst to produce the 6,6'-BINAP derivative. This preferred process is shown in detail below in Flow Sheet A.

FLOW SHEET A

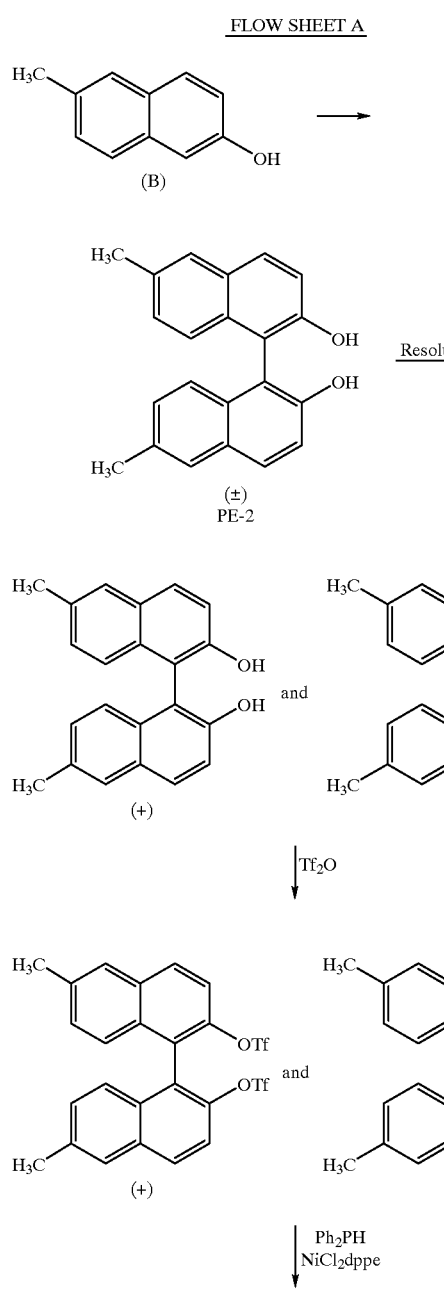

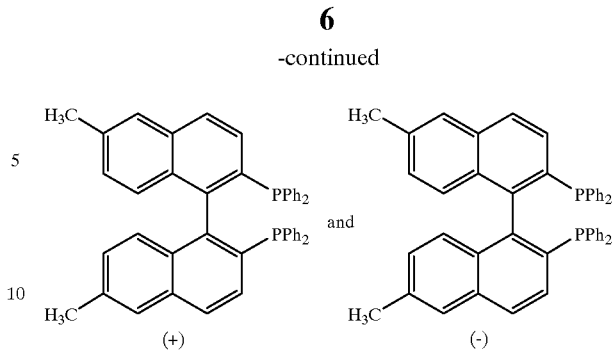

BINAP derivatives have been useful in the preparation of antibiotics, in particular, carbapenems. In many carbapenem antibiotics, a side chain is present at position 2, which contains a hydroxyalkyl-pyrrolidine group. Such hydroxyl groups can be produced by reacting a carbonyl at the appropriate position with a compound of formula 1. This reaction is typically conducted in an alcoholic solvent, and in the presence of an acid.

The invention is further described in connection with the following non-limiting examples.

Preparative Example 1

6-Methyl-2-Naphthol

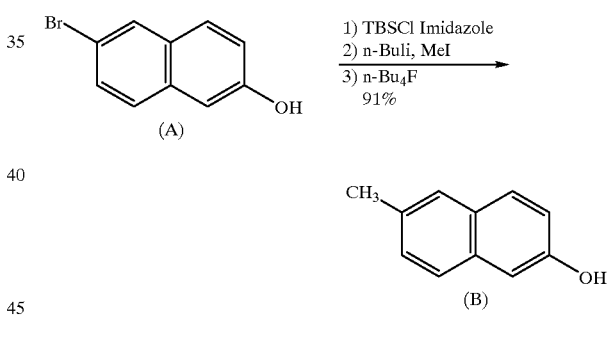

React 6-bromo-2-naphthol with t-butyl dimethylsilyl chloride and imidazole, followed by adding n-BuLi and CH₃I. Deprotect the hydroxyl group by reacting with n-Bu₄F to produce the title compound.

Preparative Example 2

6-Carbomethoxy-2-Naphthol

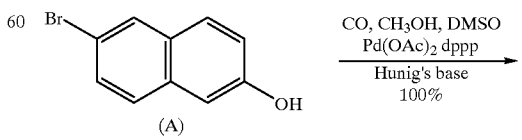

-continued

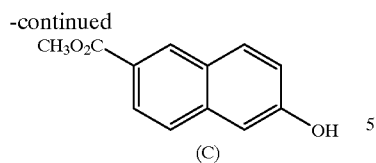

(C)

A solution of (A) (22.3 g, 100 mmoL) and Pd(OAc)$_2$, (1.12 g, 5 mmol) and dppp (2.00 g, 5 mmol) in degassed DMSO (500 mL), MeOH (150 mL) and diisopropylethylamine (77 mL) is reacted with carbon monoxide at 1.5 ATM/80° C. for 3 days. The reaction solution is diluted with ethyl acetate (EtOAc) (1.0 L) then washed with water (3×500 mL). The aqueous layers are back extracted with EtOAc (0.5 L). The EtOAc layers are concentrated to a brown solid, and purified by recrystallization in hexane to yield the product.

Preparative Example 3

7,7'-Bis(Methoxy)-2,2'-Dihydroxy-1,1'-Binaphthyl ((+)-PE-1)

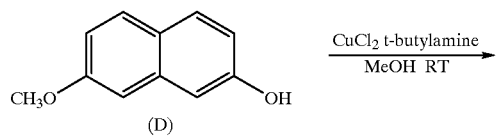

-continued

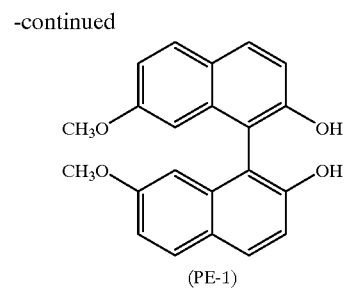

(PE-1)

A solution of (D) (10 g, 57.4 mmol) and CuCl$_2$ (15.44 g, 114.8 mmol) in degassed methanol (350 mL) is stirred while Ar is bubbled through for 15 min. t-butylamine (459 mmol, 150 mL of a 3.08 M freshly prepared solution in MeOH) was added over one hour and the reaction is stirred for 22 hrs. 350 mL of HCl 6 N and 100 mL of HCl 1 N is slowly added and the MeOH evaporated. The residue is taken up in 800 mL of EtOAc and washed with saturated NaHCO$_3$ (4×150 mL), washed with brine and dried over MgSO$_4$.

The organic layer is concentrated to an oil which is purified by silica gel chromatography using 10% EtOAc/toluene or by crystallization in hexane/toluene (8:2).

Preparative Example 4

Using the procedure set forth in Preparative Example 3, the naphol shown in column 1 is reacted to produce the bisnaphthol derivative shown in column 2.

TABLE 1

| Naphthol derivative | Bisnaphthol derivative | |
|---|---|---|
| ![B structure] (B) | ![PE-2 structure] | PE-2 |
| ![C structure] (C) | ![PE-3 structure] | PE-3* |

*Compound isolated by adding water to the solution, whereupon the desired compound formed a precipitate. Coupling reaction required a large excess of t-butylamine (8 eq.) and solvent (CH$_3$OH). Due to the insoluble nature of this compound, in almost all solvents except DMSO, the compound was prepared from the BR analog in optically pure form.

Alternative Preparative Example 4

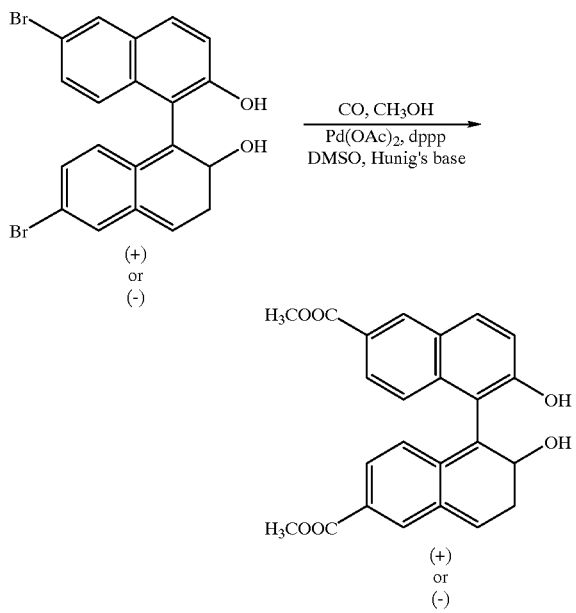

Using the procedure set forth in Preparative Example 2, Compound PE-3 can be obtained.

Preparative Example 5

Alternative Coupling Reactions

The compound in column 1 of Table 2 below can be reacted to form the binaphthyl derivative in column 2 by heating with $FeCl_3 \cdot H_2O$ (2 eq.) followed by isolation and crystallization.

TABLE 2

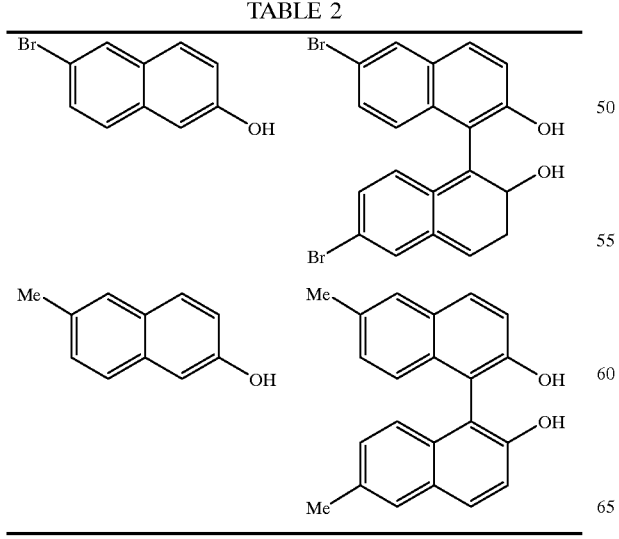

Preparative Example 6

7,7'-Bismethoxy-2,2' Ditriflate-1,1' Binaphthyl (+) or (−)(PE-4)

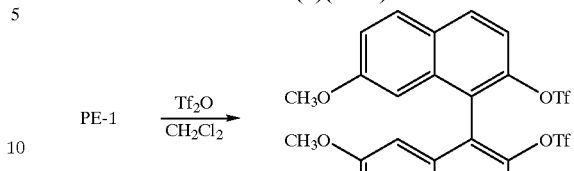

To a solution of PE-1 (7.54 g, 21.8 mmol) in 300 mL of dichloromethane is slowly added pyridine (5.28 mL, 65.3 mmol) and trifluoromethane sulfonic anhydride (8.79 mL, 52.3 mmol) at 0° C. The reaction was stired for 3 hrs and 300 mL of HCl 1N was added. The aqueous layer was extracted with 800 mL of dichloromethane and the organic layer was washed with saturated $NaHCO_3$ (2×100 mL), washed with brine, dried over $MgSO_4$ and concentrated to the title compound (12.1 g) as a powder.

Preparative Example 7

Using the procedures set forth in Preparative Example 6, the bisnaphthyl ditriflates below are prepared.

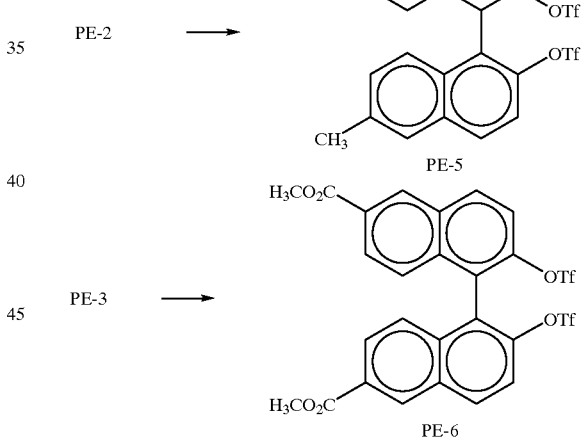

EXAMPLE ONE 7,7'-Bis(Methoxy)-Binap ((+)-(1)

![](PE-4 → with $Ph_2PH$ $NiCl_2$ dppe, DABCO DMF 100° C.)

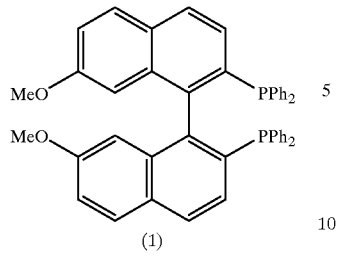

(1)

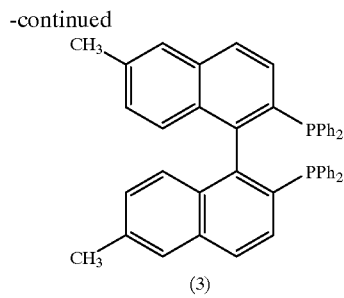

(3)

To a solution of NiCl₂ dppe (864 mg, 1.6 mmol) in DMF (15 ml) was added diphenylphosphine (0.820 ml, 4.7 mmol) at room temperature, then the resulting solution was heated at 100° C. After heating at 100° C. for 30 min., a solution of ditriflate PE-4 (5 g, 8.18 mmol) and DABCO (3.67 g, 32.8 mmol) in DMF (25 ml) was added at once and the resulting dark green solution was kept at 100° C. Two more portions of Ph₂PH were added after 1.5 h, and 4.5 h, respectively. The reaction was kept at 100° C. overnight. The reaction was cooled down to room temperature and finally cooled down to 0° C. in an ice bath. The desired product was filtered and the cake was washed with MeOH and dried under vacuum.

$^1$H NMR (250 MHz, CD₂Cl₂) δ3.12 (s, 6H), 6.05 (d, J=2.4, 2H), 7.0 (dd, J=8.97 and 2.6, 2H), 7.15 (m, 20H), 7.32 (d, J=9.6, 2H), 7.75 (d, J=8.9, 2H), 7.85 (d, J=8.4, 2H).

$^{13}$C NMR (250 MHz, CDCl₃) δ54.6, 105.6, 119.14, 127.3, 127.8, 127.97, 128.0, 128.08, 128.3, 128.6, 128.8, 129.2, 132.4, 132.6, 132.75, 132.8, 134.3, 134.35, 134.44, 134.5, 134.6, 134.79, 136.2, 136.29, 137.5, 137.7, 138.5, 138.7, 143.0, 144.0, 157.38.

$^{31}$P NMR (250 MHz, CDCl3) δ–12.95 (s, 2P).

Analysis calculated for C₄₆H₃₆O₂P₂ (682.69): C, 80.9; H, 5.23; P, 9.07.

Found: C, 80.65; H, 5.23; P, 9.01.

Melting point: (265–267)° C.

EXAMPLE TWO

Substitute NiCl₂dppp for NiCl₂dppe in the process of Example 1 to produce compound 1.

EXAMPLE THREE 6,6'-Bis(Methyl)-Binap (±)-(3)

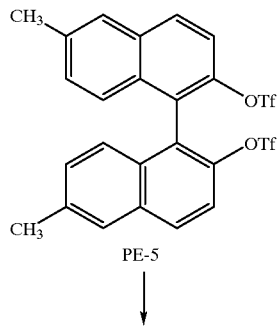

PE-5

↓

Using the procedures set forth in Example 1, replace the bismethoxy binaphthol derivative PE-4 with PE-5 and reduce NiCl₂ dppe from 0.2 eq. to 0.1 eq. to produce the title compound (3).

$^1$H NMR (250 MHz, CDCl₃) δ2.41 (s, 6H), 6.76 (d, j=1.1, 4H), 7.03–7.20 (m, 20H), 7.39 (dt, j=8.4 and 1.32, 2H), 7.61 (s, 2H), 7.79 (d, J=8.6, 2H).

$^{13}$C NMR (250 MHz, CDCl₃) δ21.58, 126.7, 127.3, 127.44, 127.48, 127.83, 127.9, 127.98, 128.18, 130.7, 131.6, 131.7, 131.8, 132.75, 132.9, 133.1, 133.5, 133.86, 133.9, 134.1, 134.14, 134.25, 134.29, 136.3, 137.8, 137.9, 137.96, 138.0, 138.03, 144.99, 145.08, 145.32, 145.58, 145.67.

$^{31}$P (250 MHz, CDCl₃) δ–14.9 (s, 2P).

Analysis calculated for C₄₆H₃₆P₂ (650.69) C, 84.9; H, 5.58; P, 9.52.

Found: C, 83.97; H, 5.46; P, 9.57.

obsvd. Melting point: (281–283)° C.

EXAMPLE FOUR 6,6'-Bis(Methylester)-Binap (±)-(4)

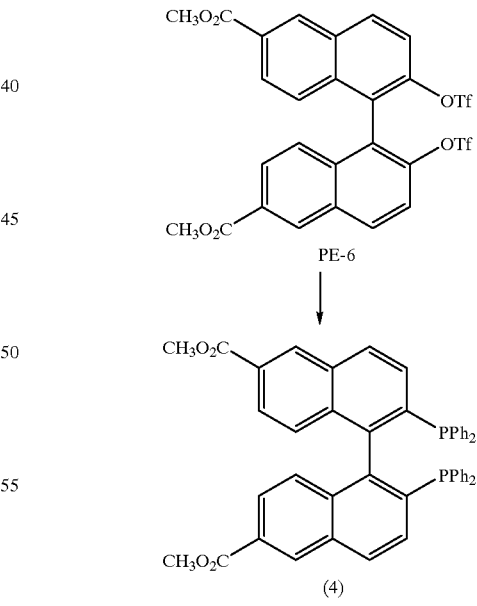

(4)

To a solution of NiCl₂ dppe (106 mg, 0.2 mmol) in DMF (2 ml) was added diphenylphosphine (0.1 ml, 0.575 mmol) at r.t. The resulting solution was then heated at 80° C. for 30 min. A solution of ditriflate PE-6 (667 mg, 1 mmol), and fresh distilled Et₃N (0.557 ml, 4 mmol) was added at once and the resulting dark green solution was kept at 80° C. Two additional portions of Ph₂PH were added at 1.5 hrs, and 4.5 hrs, respectively. The reaction was kept at 80° C. overnight and quenched with 10% aq. NH₄Cl, producing a solid. The solid was filtered, dissolved in CH₂Cl₂ and eluted on a short column with CH₂Cl₂ to produce the title compound (4).

¹H NMR (250 MHz, CDCl₃) δ3.94 (s, 6H), 6.69 (d, J=7.9, 2H), 6.98–7.23 (m, 20H), 7.40 (dd, J=8.8 and 1.8, 2H), 7.51 (dd, J=9.7 and 1.25, 2H), 8.0 (d, J=8.4, 2H), 8.57 (d, J=1.6, 2H).

¹³C NMR (250 MHz, CDCl₃) δ52.24, 125.17, 127.12, 127.64, 127.96, 128.16, 128.2, 128.27, 128.8, 129.53, 130.8, 131.1, 132.3, 132.6, 132.7, 132.9, 133.0, 134.07, 134.23, 134.41, 134.6, 135.04, 135.1, 135.2, 136.0, 136.1, 136.2, 137.1, 137.18, 137.28, 139.15, 139.24, 139.3, 143.5, 143.8, 133.1, 167.0.

³¹P NMR (250 MHz, CDCl₃) δ–13.6 (s, 2P)

Analysis calculated for $C_{48}H_{36}O_4P_2$ (738.71) C, 78.04; H, 4.91; P, 8.38.

Found: C, 77.54; H, 4.81.

obsvd Melting point: (258–258.5)° C.

What is claimed is:

1. A compound represented by the formula:

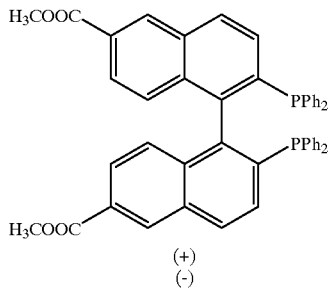

(+)
(−)

in substantially pure form or in racemic mixture.

2. A compound represented by the formula:

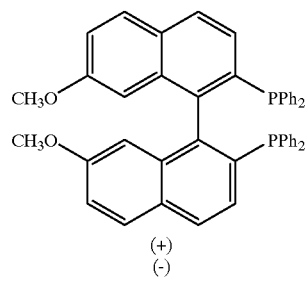

(+)
(−)

in substantially pure form or in racemic mixture.

3. A compound in accordance with claim 1 represented by the formula:

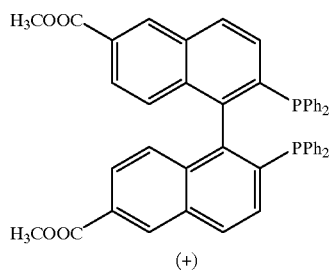

(+)

in substantially pure form.

4. A compound in accordance with claim 1 represented by the formula:

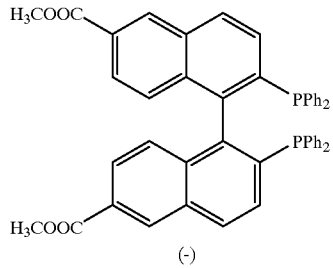

(−)

in substantially pure form.

5. A compound in accordance with claim 2 represented by the formula:

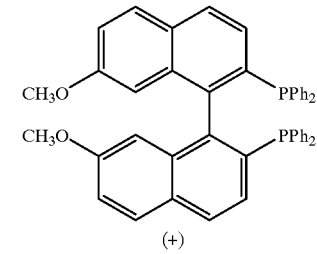

(+)

in substantially pure form.

6. A compound in accordance with claim 2 represented by the formula:

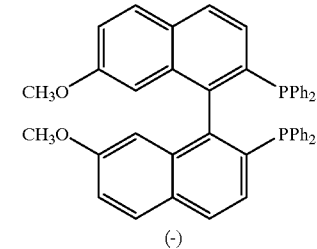

(−)

in substantially pure form.

* * * * *